United States Patent [19]

Young et al.

[11] Patent Number: 5,089,017
[45] Date of Patent: Feb. 18, 1992

[54] DRIVE SYSTEM FOR ARTIFICIAL HEARTS AND LEFT-VENTRICULAR ASSIST DEVICES

[76] Inventors: David B. Young, 1730 Bellewood Rd., Jackson, Miss. 39211-5701; Andrzej M. Pawlak, 4839 Gamber Drive, Troy, Mich. 48098

[21] Appl. No.: 298,119
[22] Filed: Jan. 17, 1989
[51] Int. Cl.$^5$ ............................................. A61F 2/22
[52] U.S. Cl. ..................................................... 623/3
[58] Field of Search ........................ 623/3; 600/16, 17
[56] References Cited

U.S. PATENT DOCUMENTS

| | | | |
|---|---|---|---|
| 2,930,324 | 10/1955 | Toulmin, Jr. | 623/3 X |
| 3,568,214 | 3/1971 | Goldschmied | 3/1 |
| 3,633,217 | 1/1972 | Lance | 3/1 |
| 3,733,616 | 5/1973 | Willis, Jr. | 3/1 |
| 3,874,002 | 4/1975 | Kurpanek | 3/1 |
| 3,974,854 | 8/1976 | Kurpanek | 137/512 |
| 4,091,818 | 5/1978 | Brownlee et al. | 128/419 PG |
| 4,143,425 | 5/1979 | Runge | 3/1.7 |
| 4,143,661 | 3/1979 | LaForge et al. | 623/3 X |
| 4,167,046 | 9/1979 | Portner et al. | 3/1.7 |
| 4,173,796 | 11/1979 | Jarvik | 3/1.7 |
| 4,195,623 | 4/1980 | Zeff et al. | 623/3 X |
| 4,213,207 | 7/1980 | Wilson | 3/1.7 |
| 4,304,238 | 12/1981 | Fischer | 128/419 PG |
| 4,453,376 | 6/1984 | Spitzer | 623/3 |
| 4,468,177 | 8/1984 | Strimling | 417/413 |
| 4,546,760 | 10/1985 | Suzuki et al. | 128/1 D |
| 4,583,525 | 4/1986 | Suzuki et al. | 128/1 D |
| 4,600,405 | 7/1986 | Zibelin | 623/3 |
| 4,621,617 | 11/1986 | Sharma | 128/1 D |
| 4,650,485 | 3/1987 | Della Sala | 623/3 |
| 4,652,265 | 3/1987 | McDougall | 623/3 |
| 4,661,107 | 4/1987 | Fink | 623/2 |
| 4,685,446 | 8/1987 | Choy | 128/1 D |
| 4,688,998 | 8/1987 | Olsen et al. | 417/356 |
| 4,697,989 | 10/1987 | Perlov et al. | 417/53 |

FOREIGN PATENT DOCUMENTS

| | | | |
|---|---|---|---|
| 0066943 | 9/1975 | Australia | 623/3 |
| 3722161 | 1/1989 | Fed. Rep. of Germany | 623/3 |
| 1444614 | 8/1976 | United Kingdom . | |

OTHER PUBLICATIONS

Mays et al., "Clinical Management of Total Artificial Heart Drive Systems", Journal of American Medical Association, Feb. 12, 1988-vol. 259, No. 6, pp. 881–885.
Lawrie, Gerald M., M. D., Editorial: "Permanent Implantation of the Jarvik-7 Total Artificial Heart: A Clinical Perspective", Journal of American Medical Association, Feb. 12, 1988-vol. 259, No. 6, pp. 892–893.
Mays et al., "Drive System Management of Emergency Conditions in Three Permanent Total Artificial Heart Patients", Reprint From vol. XXXII Trans Am Soc Artif Intern Organs, 1986, pp. 221–225.
Author Unknown, "The Critical Interval" (General Motors) Research and Development, Aug. 1987.

*Primary Examiner*—David J. Isabella
*Attorney, Agent, or Firm*—Fitch, Even, Tabin & Flannery

[57] ABSTRACT

A drive system for artificial hearts and left-ventricular assist devices. The drive system includes one or more implantable pumps driven by external electromagnets. Each pump preferably includes an armature made of a permanent magnet material having a magnetic energy product of at least about $30 \times 10^6$ Gauss Oersted, and coercivity of at least about 10 kOe.

In one embodiment of the invention, a pair of pumps are provided, with each being coupled to a respective ventricle of an artificial heart. In a second embodiment, a pair of pumps is connected to a single left-ventricular assist device.

Each pump is mounted to the pelvic bone in the vicinity of the iliac crest. Fluid communication between the pump and its associated ventricle or left-ventricular assist device is provided by a length of flexible tubing extending subcutaneously up from the pump. Means are provided to enable periodic reversal of internal system leakage, and to enable replenishment of fluid lost from the system.

Each electromagnet may be operated and powered by a plurality of rechargeable batteries and a PWM-type controller with a DC/DC converter. The electromagnets, batteries, and controller may be supported on a belt or girdle to provide a portable system, or alternatively may be mounted in a stationary support.

8 Claims, 7 Drawing Sheets

DRIVE SYSTEM FOR ARTIFICIAL HEARTS AND LEFT-VENTRICULAR ASSIST DEVICES

BACKGROUND OF THE INVENTION

The invention relates generally to artificial hearts and left-ventricular assist devices, and more particularly to drive systems for such apparatus.

Certain artificial hearts and left-ventricular assist devices such as the "Jarvik 7" heart are driven by fluid pressure, typically provided by an external pump connected to the implanted device by transcutaneous tubing. Such drive systems have various disadvantages, such as risk of infection, which become particularly problematic over the long term.

It is a general object of the invention to provide a drive system which is suitable for long-term use, without the disadvantages associated with transcutaneous tubing and wiring, and without significant generation of heat within the body.

Further objects of the invention will become apparent from the following description and the accompanying drawings.

SUMMARY OF THE INVENTION

In accordance with the invention, there is provided a drive system for artificial hearts and left-ventricular assist devices which requires no transcutaneous connection and includes one or more implantable pumps driven by external electromagnet means. Each pump preferably includes an armature made of a permanent magnet material having a high magnetic energy product of at least about $30 \times 10^6$ Gauss Oersted, and coercivity of at least about 10 kOe, in order to provide sufficient power to drive the heart under a variety of physiological conditions over a period of several years. The electromagnetic drive arrangement eliminates any need for transcutaneous tubing or other transcutaneous power connections, and requires no significant heat generation within the body.

In one embodiment, a pair of pumps are provided, with each being coupled to a respective ventricle of an artificial heart. In a second embodiment, a pair of pumps are connected to a single left-ventricular assist device. In these embodiments, the pumps are affixed to opposite sides of the pelvic bone, with each being located in the vicinity of the iliac crest.

Fluid communication between each pump and its associated ventricle or left-ventricular assist device is provided by a length of flexible tubing extending subcutaneously up from the pump. Means are provided to enable periodic reversal of internal system leakage, and to enable replenishment of fluid lost from the system.

To provide a portable system, each electromagnet may be operated and powered by a plurality of rechargeable batteries and a PWM-type controller with a DC/DC converter, with the electromagnets, batteries and controller all supported on a belt or girdle.

DETAILED DESCRIPTION OF PREFERRED EMBODIMENT

Introduction

The invention is preferably embodied in a drive system 10 which includes one or more implantable pumps 12 and external electromagnetic means 14 for driving the pumps. In accordance with a first embodiment of the invention, illustrated in FIG. 1, there is provided a pair of pumps 12, with each being coupled to a respective ventricle 24 of an artificial heart 16. In accordance with a second embodiment of the invention, such a pair of pumps may be employed as part of a left-ventricular assist device. Referring to the embodiment illustrated in FIG. 1, each pump 12 is equipped with mounting means 18, described in further detail below, which enable it to be fixed to the pelvic bone 20 in the vicinity of the iliac crest 22. Fluid communication between the pump 12 and its associated ventricle 24 is provided by a length of flexible tubing 26 extending subcutaneously upward from the pump to the respective ventricle 24. Means are provided to enable periodic recharging of the system fluid 28.

Figure 1:
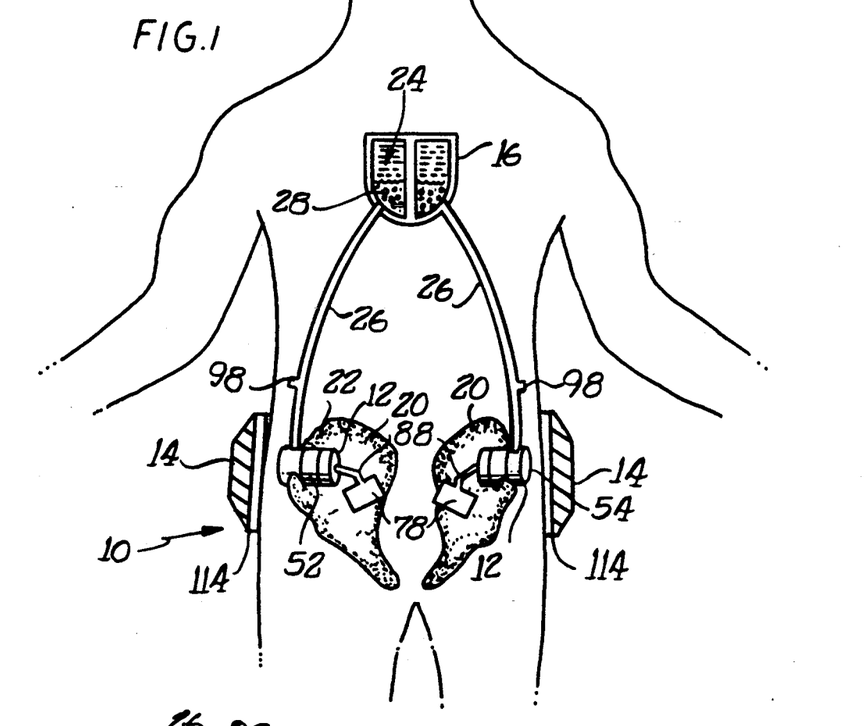
FIG. 1 is a diagrammatic view illustrating a drive system in accordance with the invention.
Figure 7:
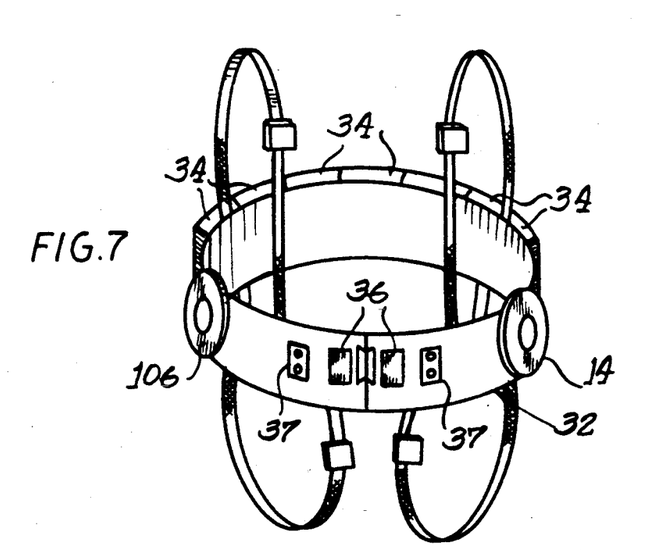
FIG. 7 is a perspective view of the belt assembly of the system of FIG. 1.
Figure 8:
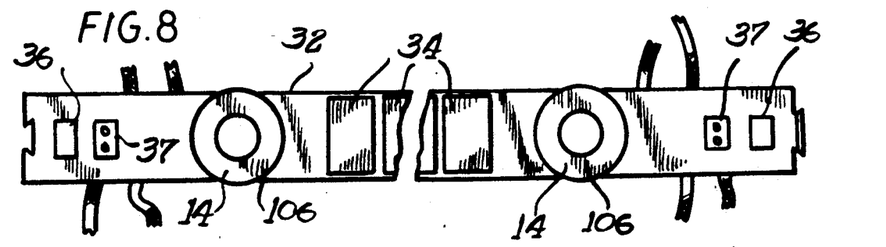
FIG. 8 is a foreshortened elevational view of the belt of FIG. 7, with the belt shown in a linear configuration, and with portions broken away.

The preferred electromagnetic means for driving the pumps comprise a pair of electromagnets 30 which are carried on a belt 32 or girdle, and which are powered and operated by a plurality of rechargeable batteries 34 and a controller 36, which includes a DC/DC converter, and switches 37 also carried thereon.

Pump and Associated Implanted Components

Figure 2:
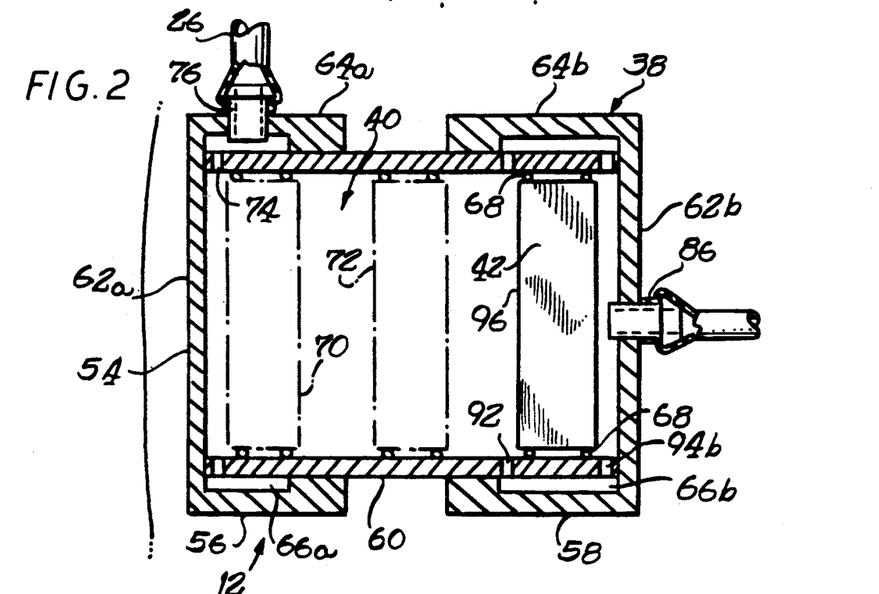
FIG. 2 is a sectional, side elevational view of one of the pumps of the system of FIG. 1.

The preferred pump comprises a housing 38 defining a pumping chamber 40 and a piston 42 displaceable in reciprocating rectilinear travel within the housing 38. The housing 38 has a generally cylindrical exterior surface 44 and includes a pair of axially-spaced nuts 46 in threaded engagement with the exterior surface 38, and a bridge 48 fixed to the exterior of the housing and adapted to be fixed to the cortical bone 50 adjacent the iliac crest. The pump 12 is implanted by cutting a downwardly extending slot 52 in the iliac crest, inserting the housing 38 so that it extends through the slot substantially perpendicular to the crest so that it is partially supported thereby. The nuts are then tightened against the opposite sides of the crest and the bridge is screwed to adjacent cortical bone to stabilize the pump. The end 54 of the pump 12 adjacent the electromagnet, hereinafter, "the proximal end", is located no more than 10 mm from the outer surface of the epidermis.

The housing herein is a three-piece assembly comprising a proximal head 56, a distal head 58, and a substantially cylindrical sleeve 60 extending between the two heads. The heads 56, 58 and sleeve 60 are constructed of a nonmagnetic metal or suitable polymer.

Each of the heads 56, 58 comprises a substantially circular, planar end wall 62a, 62b with an annular wall 64a, 64b extending inward therefrom outside of the sleeve 60 and sealed thereto. Each of the annular walls 64a, 64b has an interior annular channel 66a, 66b formed therein adjacent the interior of the end wall. Each of the channels 66a, 66b cooperates with the exterior of the sleeve 60 to define a plenum. The heads are sealed against the cylindrical sleeve around the ends of the sleeve and around the exterior of the sleeve.

The piston 42 is movably sealed to the interior of the pumping chamber 40 by one or more sealing rings 68, and normally reciprocates in a pumping stroke between a first position 70 near the proximal end of the sleeve and a second position 72 near the center of the sleeve. The end positions 70 and 72 of the normal stroke of the piston are shown in broken lines in FIG. 2.

During systole, the piston 42 travels toward the proximal end of the cylinder, driving the fluid out of the pumping chamber 40 through a plurality of ports 74 formed radially through the sleeve near its proximal end into the channel 66a, and thence through an additional port 76 into the tubing 26. Port 76 is equipped with a suitable tubing connector. During diastole, the fluid flows in the opposite direction through the same path.

Figure 3:
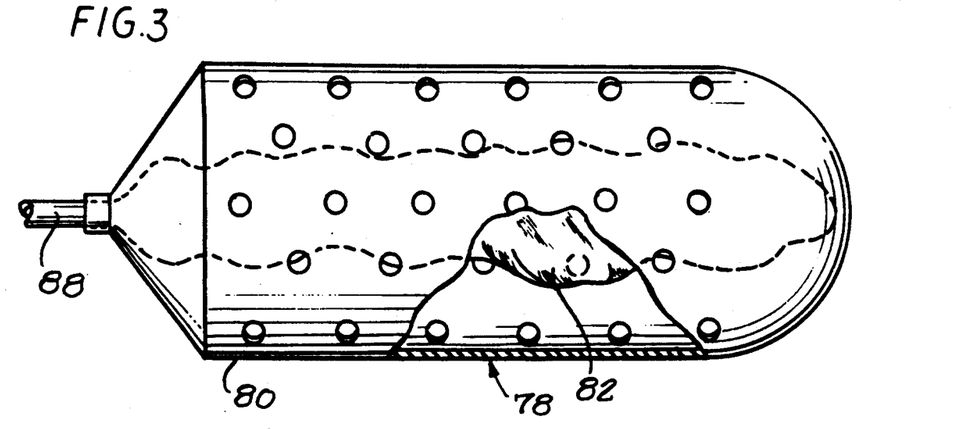
FIG. 3 is a side elevational view, shown with a portion broken away, illustrating a fluid reservoir of the system of FIG. 1.

To provide substantially constant pressure on the distal side of the piston, a reservoir 78 of fluid of variable volume and substantially constant pressure is maintained in communication with the distal end of the pumping chamber. The fluid reservoir 78, illustrated in detail in FIG. 3, comprises a fenestrated canister 80 having a flexible bag 82 contained therein to accommodate fluid. The canister 80 is contained in the patient's abdominal cavity 84, and accordingly, the pressure within the canister 80 is substantially constant at one atmosphere. The reservoir 78 communicates with the distal end of the pumping chamber through a port 86 in the end wall of the distal head 58 and a length of tubing 88 attached thereto.

Figure 11:
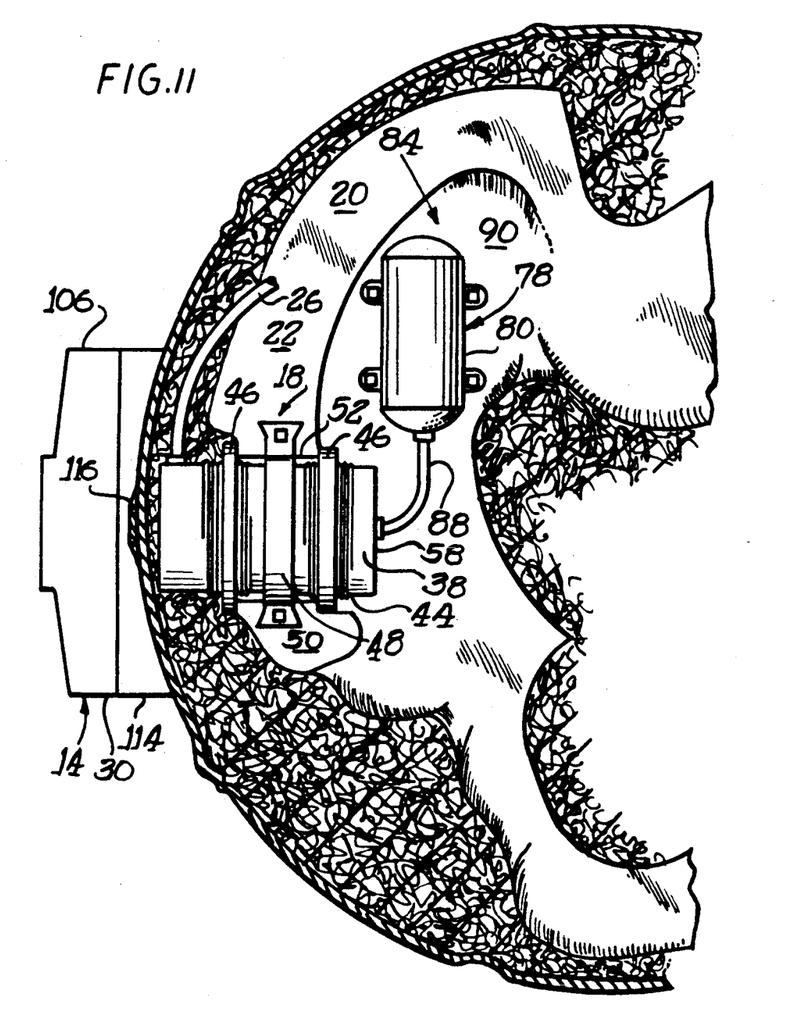
FIG. 11 is a plan view of the pump assembly of the system of FIG. 1, shown in its implanted configuration adjacent the iliac crest, with portions of surrounding tissue shown in section.

As illustrated in FIGS. 1 and 11, the reservoir 78 is preferably affixed to the inner surface 90 of the iliac bone. The flexible internal bag 82 is preferably made of polyurethane and has a volume of about 200 ml. The rigid fenestrated support permits the bag to expand and contract freely while preventing impingement of abdominal contents onto the flexible bag.

During normal operation, the pressure differential across the piston 42 will be greater during systole than during diastole. This may result in a slight gradual leakage of fluid past the piston 42 from the proximal end of the pumping chamber 40 to the distal end thereof. To enable internal reversal of such leakage, means are provided to enable fluid periodically to bypass the piston and flow from the distal end to the proximal end. For this purpose, the sleeve 60 has two sets of bypass ports 92 and 94 disposed near its distal end, spaced sufficiently from one another to enable the piston to be positioned therebetween. The bypass ports 92 and 94 are connected to one another outside of the pumping chamber 40 by the channel 66b. Periodically, the piston 42 may be displaced beyond the distal end position 72 of its normal stroke and stopped for a short period of time between the bypass ports 92 and 94, in the position 96 shown in solid lines in FIG. 2, thereby enabling bypass flow from the distal end to the proximal end. The frequency of the bypass operation is determined by the amount of leakage. For purposes of example, the controller 36 may conduct the bypass operation once after every 10,000 cycles.

During the bypass operation, the piston is held by the control system 36 at the bypass position 96 for two seconds. During that time, blood fills the associated ventricle 24 of the artificial heart, thereby displacing all of the working fluid 28 from the ventricle. This makes the refilling procedure reproducible, by defining a fixed volume (within the tubing 26 and pumping chamber) between the piston and the ventricle, filled with fluid at a known pressure (1 atm.) Preferably, an alarm associated with the control system sounds to warn the patient each time the refilling procedure is about to take place.

Figure 4:
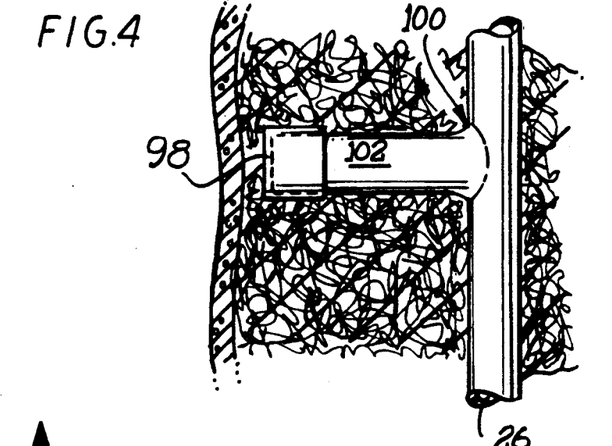
FIG. 4 is a side elevational view of a port to enable replenishment of fluid in the system of FIG. 1.
Figure 5:
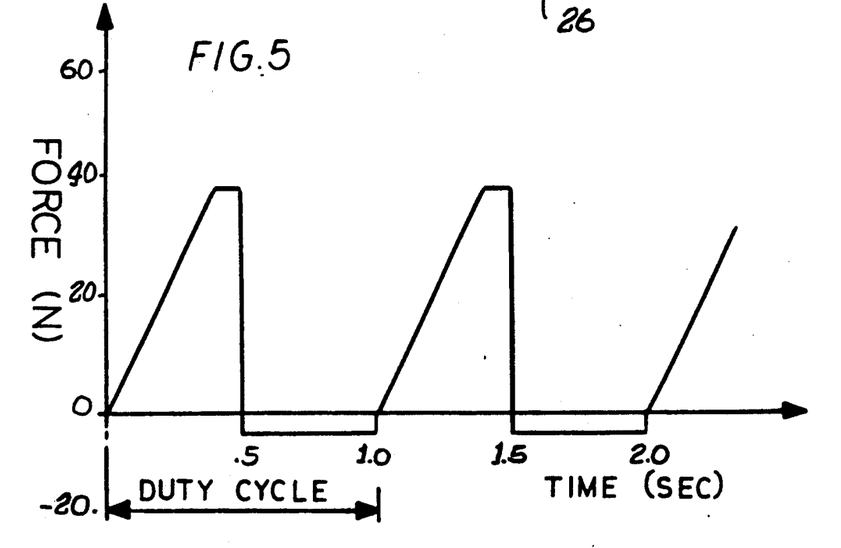
FIG. 5 is a plot of the force developed by the pump of FIG. 2, shown as a function of time, during one mode of operation.
Figure 6:
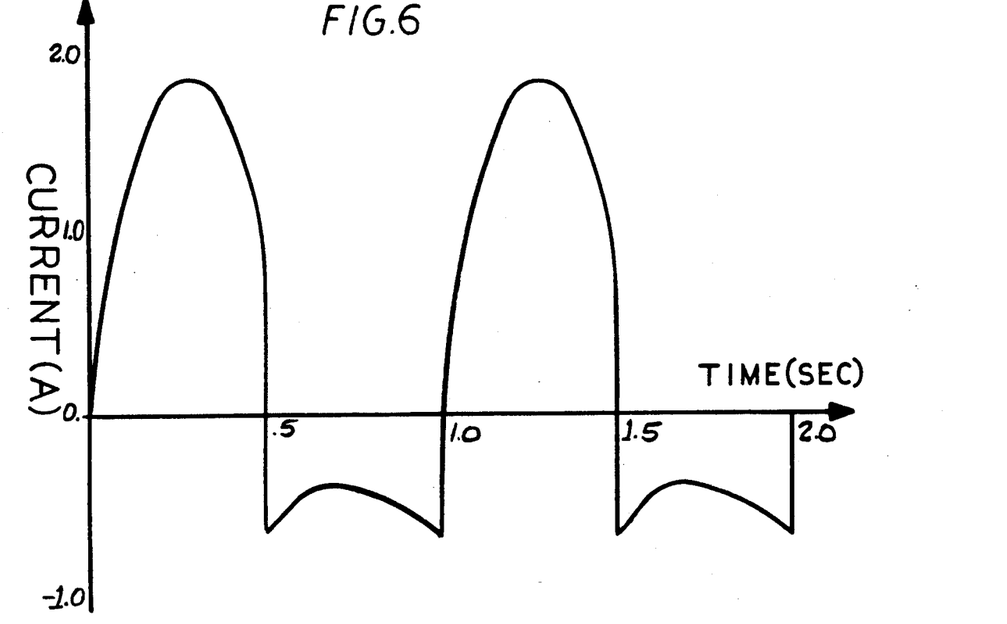
FIG. 6 is a plot of current supplied to an electromagnet in the system of FIG. 1, shown as a function of time, during a 60 beat per min. mode of operation.

Over a period of several months or years, a significant portion of the fluid 28 may escape from the system entirely, and at some point, introduction of a quantity of replacement fluid into the system may be necessary. To this end, injection ports 98 are provided in each of the tubes connecting the pumps 12 with the artificial heart chambers.

The tubing 26 for each pump 12 is tunneled subcutaneously from the pump into the chest cavity and into connection with the artificial heart 16. The tubing 26 is fitted with a T-connection 100 which provides a short tubing segment 102 extending toward the epidermis, and with the puncture port 98 at its end, accessible to hypodermic needles passed through the skin. The port 98 may also be used to monitor pressure in the system during normal operation, and enable emergency connection of an external pumping system in the event of failure of some part of the apparatus merely by making a small incision through the skin.

It is desirable that the working fluid 28 in the system be nontoxic and nonmagnetic. To this end, the preferred working fluid is sulfur hexafluoride.

The preferred piston 42 comprises a permanent magnet made of an iron-boron-neodymium material. This material has a magnetic energy product of approximately $35 \times 10^6$ Gauss Oersted, and a coercivity of about 12 kOe. The magnet has its poles at its respective proximal and distal ends, and is coated with a nonmagnetic metal or a suitable polymer.

Electromagnet Assembly and Controller

Figure 9:
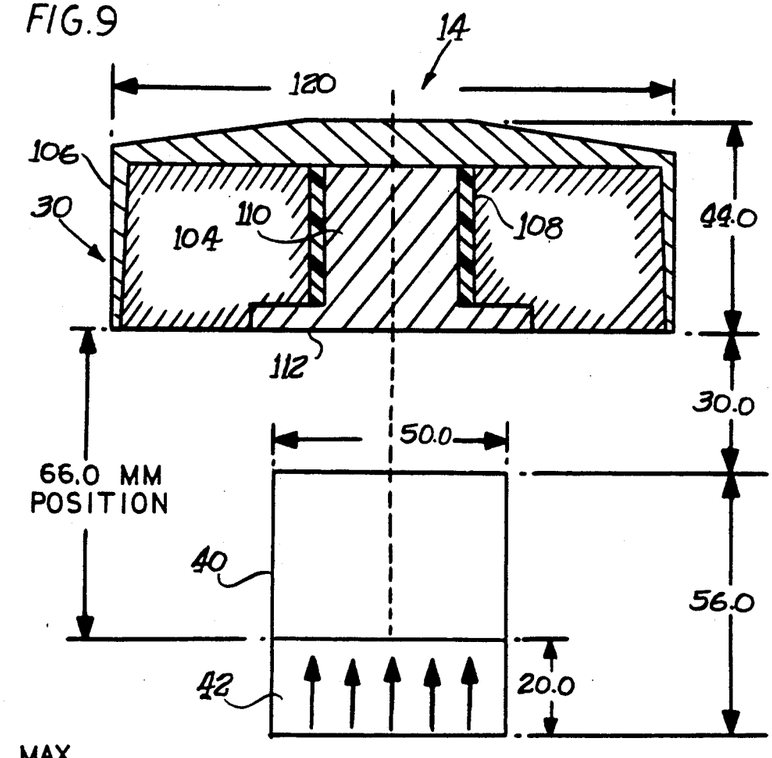
FIG. 9 is a diagrammatic view illustrating the electromagnet, pumping chamber, and piston of the system of FIG. 1.

The illustrated electromagnet assembly comprises a coil 104 supported in a cup-shaped housing 106, wound around a nylon bobbin 108. The bobbin 108 is supported on a central pole 110 which extends through the center of the bobbin and has a shoe 112 at its inner end. The central pole 110 is attached to the housing by screws. The pole 110 is made of vanadium permendur, and the housing 106 is made out of magnetic 1008 steel. The shoe 112 is optimized for maximum force, and has an outer diameter larger than that of the permanent magnet. All of the magnetic wall cross sections are dimensioned to minimize their weight while providing optimum magnetic properties for the flux by avoiding local saturations.

In an alternative embodiment, the bobbin may be by employing bobbinless precision-wound coil.

As illustrated in FIG. 11, the magnet assembly preferably includes a semirigid pad 114 contoured to fit between the body and the electromagnet assembly 30 to perform three functions: 1) insulating the epidermis thermally so as to avoid unacceptably high heat transfer from the magnet 30 thereto; 2) distributing the compressive force applied to the tissue between the pump 12 and the electromagnet 30, thereby avoiding unacceptably high mechanical stress concentrations; and 3) providing mechanical stability for the electromagnet 30 to facilitate maintenance of the proper alignment and spatial relationship between the electromagnet 30 and the pump 12.

The source of electric power for the electromagnet 30 is preferably a plurality of rechargeable batteries 34 having high-energy density. The illustrated system employs seven series-connected 10 volt silver-zinc batteries having an energy density of about 35 Wh/lb.

The electromagnet is controlled by a PWM-type controller 36. The controller 36 receives information as to the position of the piston 42 from a sensor 116, and includes a conventional DC/DC converter to vary the voltage across the electromagnet within a range of about $-24$ volts to $+70$ volts, in order to satisfy the applicable performance criteria for the pump 12. The piston position sensor 116 is attached by adhesive to the skin adjacent the proximal head of the piston.

Operation

Figure 12A:
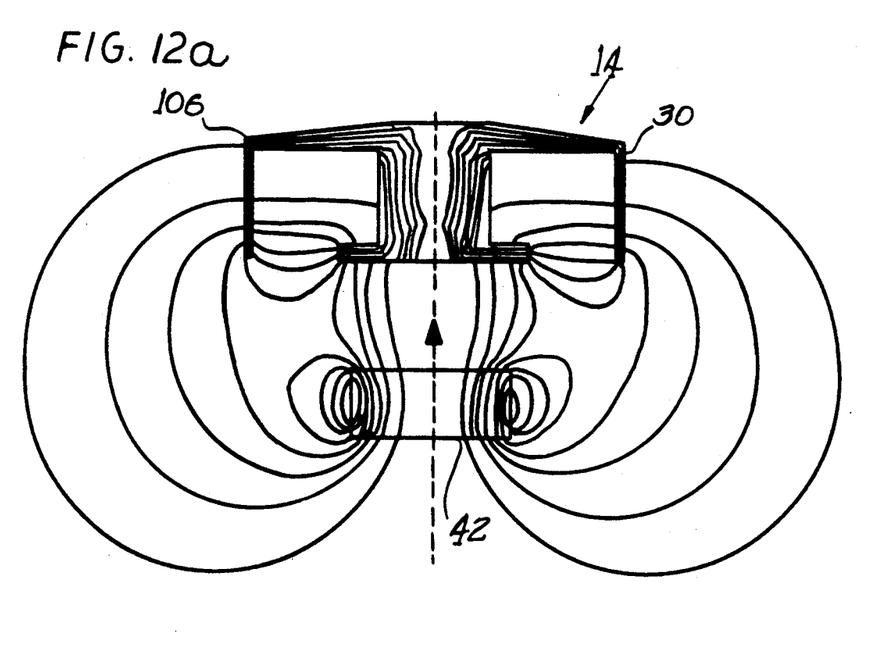
FIG. 12a is a diagrammatic representation of magnetic flux during attraction.

During normal operation, the electromagnet coil 104 is excited at a rate of, e.g., 60 cycles per minute, to alternately attract and repulse the permanent magnet armature or piston 42. Systole begins with the piston 42 at the distal end of its stroke. The energization of the coil 104 at this point produces flux lines as illustrated in FIG. 12a attracting the permanent magnet toward the proximal end of the pumping chamber 40. As the piston 42 travels in this direction, the attractive force increases linearly, which increases the fluid pressure linearly within the chamber 40. The working fluid 28 is driven out of the pump 12, through the tubing 26, and into the ventricle 24 of the artificial heart. This in turn pumps blood out of the artificial heart ventricle 24.

The duration of systole is about 33% of the period of the cycle. The current is reversed as the piston reaches the proximal end of its stroke.

Figure 12B:
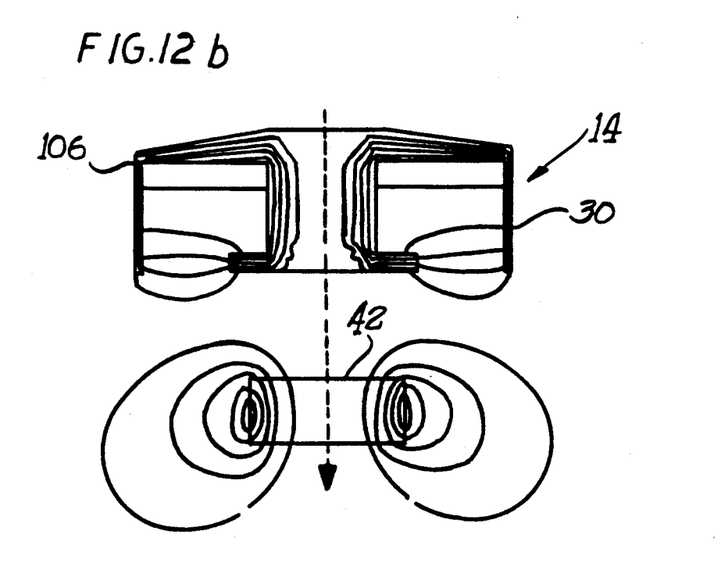
FIG. 12b is a diagrammatic representation of magnetic flux during repulsion.

The flux lines resulting from reversal of the current are illustrated in FIG. 12b. As the piston reverses direction and begins diastole, starting back toward the distal end of its stroke, the pressure differential across the piston is relatively low. The working fluid 28 flows out of the artificial heart chamber, downward through the tube 26 and back into the pumping chamber 40, filling the pumping chamber. The repulsive force aids in returning the piston to the distal end of its stroke and thereby enables higher heart rates than could otherwise be achieved. The current is again reversed to a positive value as the piston 42 approaches the distal end of its stroke.

Figure 10:
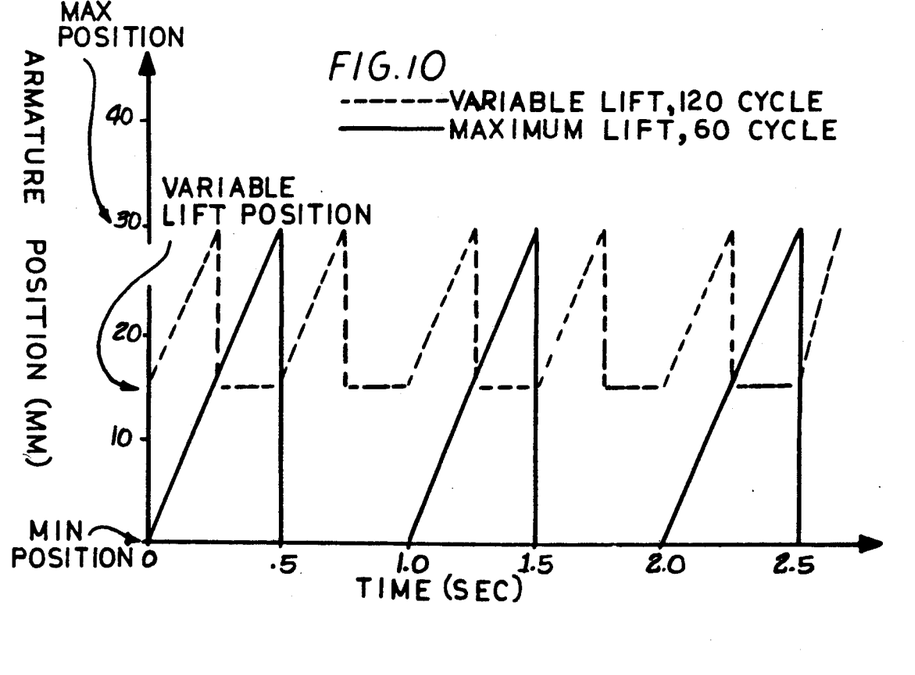
FIG. 10 is a plot of armature (piston) position as a function of time, shown in two different modes, with a maximum lift, 60 cycle/min. mode being shown in a solid line, and a variable lift, 120 cycle/min. mode, being shown in a broken line.

When the body needs increased cardiac output, the rate of venous flow into the heart increases. This increases pressure in the pumping chamber 40 during the diastolic stroke, which increases the velocity of the piston 42. The control system 36 triggers the beginning of each systolic stroke when the piston 42 reaches a predetermined point corresponding to the end of the diastolic portion of the stroke. Thus, the increased piston velocity during diastole increases the pump frequency, thereby increasing the rate of blood flow in response to increased physiological requirements.

The above-described method of control adjusts blood flow rate while maintaining a relatively constant stroke, changing only the pump frequency. As a secondary measure, the control system 36 increases stroke length when the requirements of the body cannot otherwise be met. Lengthening the stroke is a secondary measure because it decreases system efficiency due to increased distance between the piston 42 and the electromagnet 30.

Dimensions

For purposes of example, the dimensions and specific design parameters of a portable artificial heart drive system embodying the invention are set forth below:

| | |
|---|---|
| Pump | |
| Piston diameter | 50 mm |
| Piston thickness | 20 mm |
| I.D. of cylinder sleeve | 52 mm |
| Length of cylinder sleeve | 70 mm |
| Maximum stroke volume | 70 ml |
| Pressure in chamber during systole | 150 mmHg |
| Tubing I.D. | 6 mm |
| Radial dimension of plena | 4 mm |
| Design pressure of cylinder assembly | 400 mmHg (8 psi) |
| Maximum force required of pump | 40 N |
| Maximum force required during diastole | 4 N |
| Duration of peak force during systole | 20% of cycle |
| Frequency range | 50–200 cycles/min. |
| Portable Components | |
| Total mass of portable components | 8 kg |
| Total volume of portable components | 2 L |
| Discharge time of batteries at maximum power | 4 hours |
| Battery mass | 2.5 kg total |
| Battery volume | 900 cc |
| Range of voltage applied to electromagnet | −24 to +70 v |
| Controller and DC/DC converter | |
| Average current | 1.26 amps |
| Average power | 50 w |
| Average efficiency | 84% |
| Volume | 65 cc |
| Converter mass | 0.3 kg |
| Electromagnet | |
| Distance between electromagnet and cylinder | 30 mm |
| Permanent magnet mass | 300 g |
| Electromagnet mass | 2.5 kg |
| Electromagnet volume | 500 cc |
| Maximum time average power | 42 Watts |
| Maximum time average current | 1.06 amps |
| Maximum current | 1.8 amps |
| Maximum temperature rise | 80° C. |

| -continued | |
|---|---|
| Minimum thickness of insulating pad | 10 mm |
| Maximum electromagnet surface temperature | 70° C. |
| Maximum temperature on skin adjacent electromagnet | 42° C. |

Left-Ventricular Assist Device

Figure 13A:
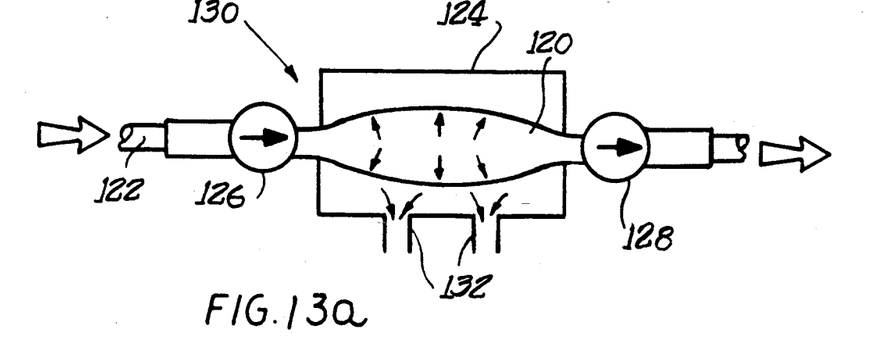
FIG. 13a is a diagrammatic view of a left-ventricular assist device for use in combination with a drive system in accordance with a second embodiment of the invention, shown during a first phase of a pumping cycle.
Figure 13B:
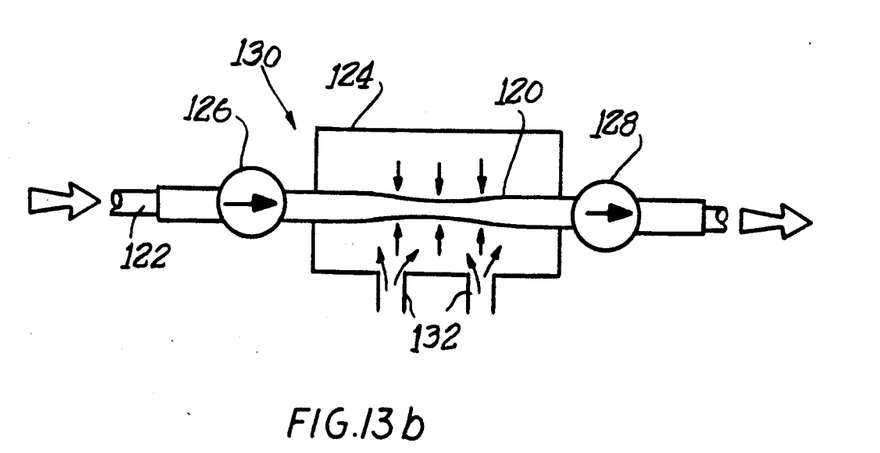
FIG. 13b is a second diagrammatic view of the device of FIG. 13a, shown during a second phase of the cycle.

An embodiment of the invention in which the pump of the invention is employed to drive a left-ventricular assist device 130 is described below.

Referring to FIGS. 13a and 13b, the left-ventricular assist device comprises a compliant blood tube 120 which is connected to the aorta 122 to receive flow therefrom; a pneumatic chamber 124 surrounding the blood tube; and a pair of one-way valves 126 and 128, one at each end of the tube 120. Contraction of the left ventricle of the patient's heart sends a pulse of blood through the aorta 122 into the compliant tube 120. In response, the compliant tube 120 expands to a predetermined maximum, then begins to contract. An artificial increase in pneumatic chamber pressure is then provided to accelerate contraction of the tube 120 and thereby increase the blood pressure and flow rate downstream.

The artificial increase in pneumatic chamber pressure is provided in this embodiment by a drive system substantially identical to that described above in connection with the artificial heart 16, except as to the operation of the controller 36. In the case of the left-ventricular assist device, the controller must operate the pump in timed relation with the patient's heart, rather than generating its own rhythm. The achievement of the required timed relationship is accomplished via sensing of piston position.

The pneumatic chamber 124 is of fixed volume, and accordingly the expansion of the compliant tube 120 decreases the volume and increases the pressure of the fluid in the pneumatic chamber. The pneumatic chamber is connected to tubing 132 leading a pair of pumps operating in parallel, one implanted on each iliac crest as described above.

Thus, expansion of the compliant tube 120 displaces the piston of each pump toward the distal end of its pumping chamber, and the piston continues to travel inwardly until the expansion of the tube 120 has peaked. As the compliant tube 120 begins to contract, the piston reverses direction. When the sensor detects reversal of the piston movement, the controller initiates a compression cycle, activating the electromagnet to attract the piston to the proximal end of the cylinder, accelerating contraction of the compliant tube 120. When the piston reaches the proximal end of its stroke, the current in the electromagnet is reversed to provide a slight repulsive force, and the next cycle begins, with expansion of the compliant tube again driving the piston away from the proximal end of the pumping chamber. As noted above, two pumps are employed, with each supplying half of the stroke volume required to operate the left-ventricular assist device.

Conclusion

From the foregoing it should be appreciated that the invention provides novel and useful means for driving implanted artificial blood-pumping apparatus. The invention is not limited to the embodiments described above, or to any particular embodiments, but rather is described in the following claims.

What is claimed is:

1. Apparatus for driving an implanted blood-pumping mechanism which is powered by fluid pressure, said apparatus comprising:

an implantable drive pump for mounting internally of the human body, comprising a housing defining a pump chamber, and a movable element supported in said housing to effect pumping of fluid into and out of said pumping chamber, said movable element including a permanent magnet;

a conduit communicating with said pumping chamber to permit flow of fluid between said drive pump and said implanted blood pumping mechanism;

an electromagnet for mounting externally of the human body to apply magnetomotive force to said permanent magnet and thereby drive said movable element;

a source of electrical power for said electromagnet; and control means connected to said source of electrical power and to said electromagnet, to regulate said magnetomotive force in such a manner as to effect pumping of said fluid by said drive pump so as to drive said implanted blood-pumping mechanism;

whereby said implanted blood-pumping mechanism may be driven and controlled without transcutaneous connections.

2. Apparatus in accordance with claim 1 wherein said movable element is a reciprocable piston which travels in a rectilinear stroke between a distal position and a proximal position relative to said electromagnet.

3. Apparatus in accordance with claim 2 wherein said control means comprises means for sensing piston position, means for effecting application of attractive force to said piston when said piston reaches said distal position, and means for effecting application of repulsive force to said piston when said piston reaches said proximal position.

4. Apparatus in accordance with claim 2 wherein said control means comprises means for sensing physiological need for increased blood flow, and means for increasing blood flow in response thereto by first increasing the rate of reciprocation of said piston up to a maximum rate, and if said need continues, secondarily increasing the length of the stroke of said piston.

5. Apparatus in accordance with claim 1 further comprising a belt support to be worn by the recipient of said artificial blood pumping mechanism to support the electromagnet, the source of electrical power, and the control means so that said apparatus may be conveniently carried by said recipient as a portable system.

6. Apparatus in accordance with claim 1 wherein said movable element is a reciprocable piston movable in a predetermined pumping stroke within said pumping chamber through a normal range of positions, and wherein said housing contains means to permit fluid to bypass said piston when said piston is moved to a predetermined position beyond said normal range of positions.

7. An implanted blood-pumping mechanism and drive apparatus therefor;

said implanted blood-pumping mechanism comprising means for containing blood, means for containing reciprocating working fluid, and means responsive to said reciprocating working fluid to effect pumping of the blood through said means for containing blood;

said drive apparatus comprising an implantable drive pump for mounting internally of the human body, comprising a housing defining a pumping chamber, and a piston supported in said housing and movable in a rectilinear pumping stroke between a proximal position and a distal position to effect reciprocation of working fluid into and out of said pumping chamber, said piston including a permanent magnet;

a conduit providing communication of reciprocating fluid between said pump and said implanted blood-pumping mechanism;

an electromagnet for mounting externally of the human body to apply magnetomotive force to said permanent magnet and thereby drive said piston;

a source of electrical power for said electromagnetic;

control means connected to said source of electrical power and to said electromagnet, to regulate said magnetomotive force in such a manner as to effect pumping of said fluid by said drive pump so as to drive said implanted blood-pumping mechanism, said control means comprising means for sensing physiological need for changes in blood flow rate, and means for adjusting blood flow rate in response thereto by first varying the rate of reciprocation of said piston up to a predetermined limit, and if said need continues, secondarily adjusting the length of the stroke of said piston; and a belt support to support the electromagnet, the source of electrical power, and the control means so that said drive apparatus may be conveniently carried as a portable system;

said control means further comprising means to shift said piston periodically to a predetermined position beyond said distal position, said housing containing means to permit working fluid to bypass said piston when said piston is moved to said predetermined position beyond said distal position; and said conduit having a fluid injection port disposed thereon to permit periodic replenishment of working fluid.

8. A left ventricular assist device for implantation in a human body comprising a compliant tube for receiving blood from the aorta, a pair of one-way valves, one of said valve located at each end of said compliant tube, and a pneumatic chamber surrounding the tube and sealed thereto;

an implantable drive pump sized for mounting internally of the human body, said drive pump including a housing defining a pumping chamber, and a movable element supported in said housing to effect pumping of fluid into and out of said pumping chamber, said movable element including a permanent magnet;

a conduit communicating with said pumping chamber to permit flow of fluid between said drive pump and said left ventricular device, said conduit establishing communication between said pumping chamber and said pneumatic chamber;

an electromagnet for mounting externally of the human body to apply magnetomotive force to said permanent magnet and thereby drive said movable element;

a source of electrical power for said electromagnet; and control means connected to said source of electrical power and to said electromagnet, to regulate said magnetomotive force insuch a manner to effect pumping of said fluid by said drive pump so as to drive said left ventricular device, said control means including a sensor for sensing contraction of said compliant tube following expansion thereof due to reception of bleood from the aorta and initiation of pumping cycle in response thereto so as to increase pressure in said pneumatic chamber and accelerate contraction of said compliant tube;

whereby said left ventricular device may be driven and controlled without transcutaneous connections.

* * * * *